United States Patent [19]

Rowden et al.

[11] Patent Number: 5,409,496
[45] Date of Patent: Apr. 25, 1995

[54] UTERINE MANIPULATOR WITH LOCKING MECHANISM

[75] Inventors: Jimmy M. Rowden, Olathe, Kans.; Robert E. O'Donnell, Kansas City, Mo.

[73] Assignee: Blairden Precision Instruments, Lenexa, Kans.

[21] Appl. No.: 106,521

[22] Filed: Aug. 16, 1993

[51] Int. Cl.⁶ .............................................. A61B 17/42
[52] U.S. Cl. .................................. 606/119; 606/193; 128/17; 128/20
[58] Field of Search .............. 606/119, 193; 604/55; 128/17, 20

[56] References Cited

U.S. PATENT DOCUMENTS

| | | |
|---|---|---|
| 1,856,295 | 5/1932 | Sovatkin . |
| 2,186,143 | 1/1940 | Neugass . |
| 2,456,806 | 12/1948 | Wolffe . |
| 3,131,690 | 5/1964 | Innis et al. . |
| 3,153,267 | 10/1964 | Cowland, Jr. . |
| 3,196,865 | 7/1965 | Rose .................................... 128/20 |
| 3,749,088 | 7/1973 | Gauthier ............................. 128/20 |
| 3,766,909 | 10/1973 | Ozbey . |
| 3,877,433 | 4/1975 | Librach . |
| 3,948,270 | 4/1976 | Hasson . |
| 4,022,208 | 5/1977 | Valtchev . |
| 4,066,071 | 1/1978 | Nagel . |
| 4,085,756 | 4/1978 | Weaver . |
| 4,323,057 | 4/1982 | Jamieson . |
| 4,430,076 | 2/1984 | Harris . |
| 4,562,832 | 1/1986 | Wilder et al. . |
| 4,597,030 | 6/1986 | Brody et al. . |
| 4,627,421 | 12/1986 | Symbas et al. . |
| 4,775,362 | 10/1988 | Kronner ............................. 604/55 |
| 4,996,974 | 3/1991 | Ciarlei . |
| 4,997,419 | 3/1991 | Lakatos et al. .................... 604/55 |
| 5,104,377 | 4/1992 | Levine ................................ 604/55 |
| 5,195,964 | 3/1993 | Khetzky et al. .................... 604/55 |
| 5,232,443 | 8/1993 | Leach ................................ 128/20 |
| 5,237,985 | 8/1993 | Hodgson et al. .................. 128/20 |
| 5,242,240 | 9/1993 | Gorham ........................... 128/20 |
| 5,273,026 | 12/1993 | Wilk ................................... 128/20 |

FOREIGN PATENT DOCUMENTS 2078526 1/1982 United Kingdom .

Primary Examiner—C. Fred Rosenbaum
Assistant Examiner—Perry E. Van Over
Attorney, Agent, or Firm—Hovey, Williams, Timmons & Collins

[57] ABSTRACT

A uterine manipulating device is provided which provides an improved handle and locking element for holding the handle in a desired position relative to the frame to which it is pivotally connected. The locking element may include a latch element for holding the handle relative to the frame in a selected one of a plurality of slots defined in the frame. Alternatively, the locking element may include a clamp for permitting the handle to be held relative to the frame in any desired position through its range of motion, The inventor hereof also includes a method of supporting a uterine manipulator during surgery including supporting the manipulator by flexible material passed through the handle and tied or otherwise attached to the legs of the patient.

2 Claims, 4 Drawing Sheets

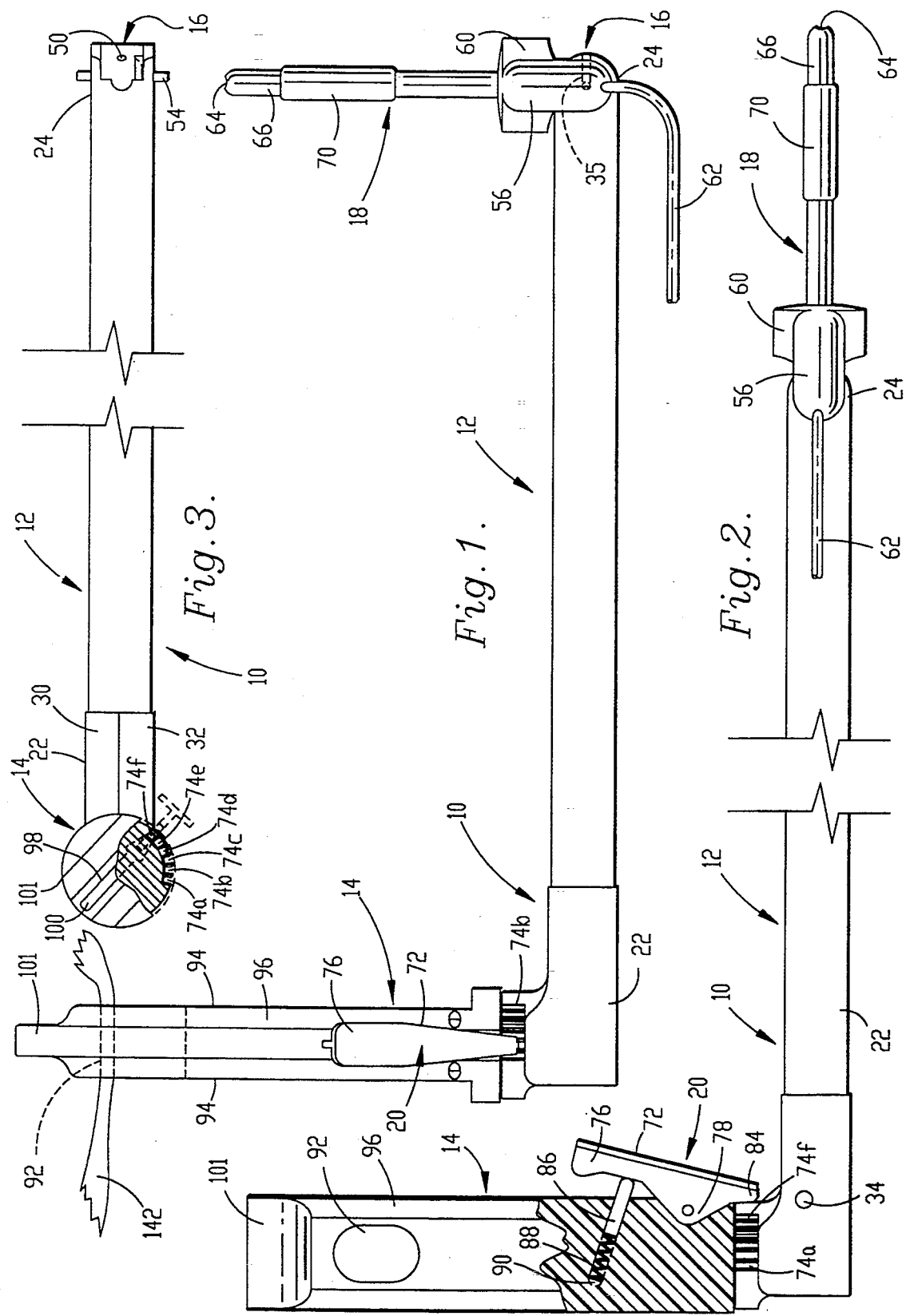

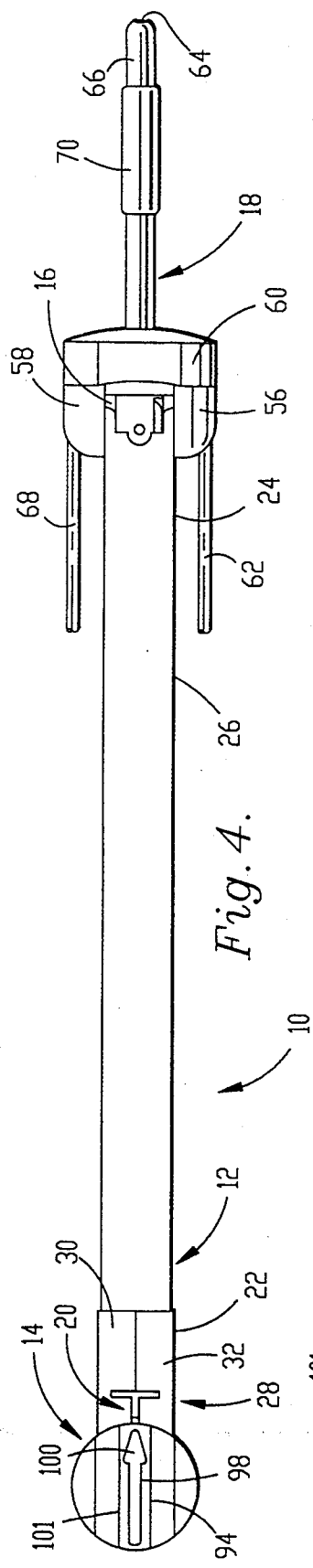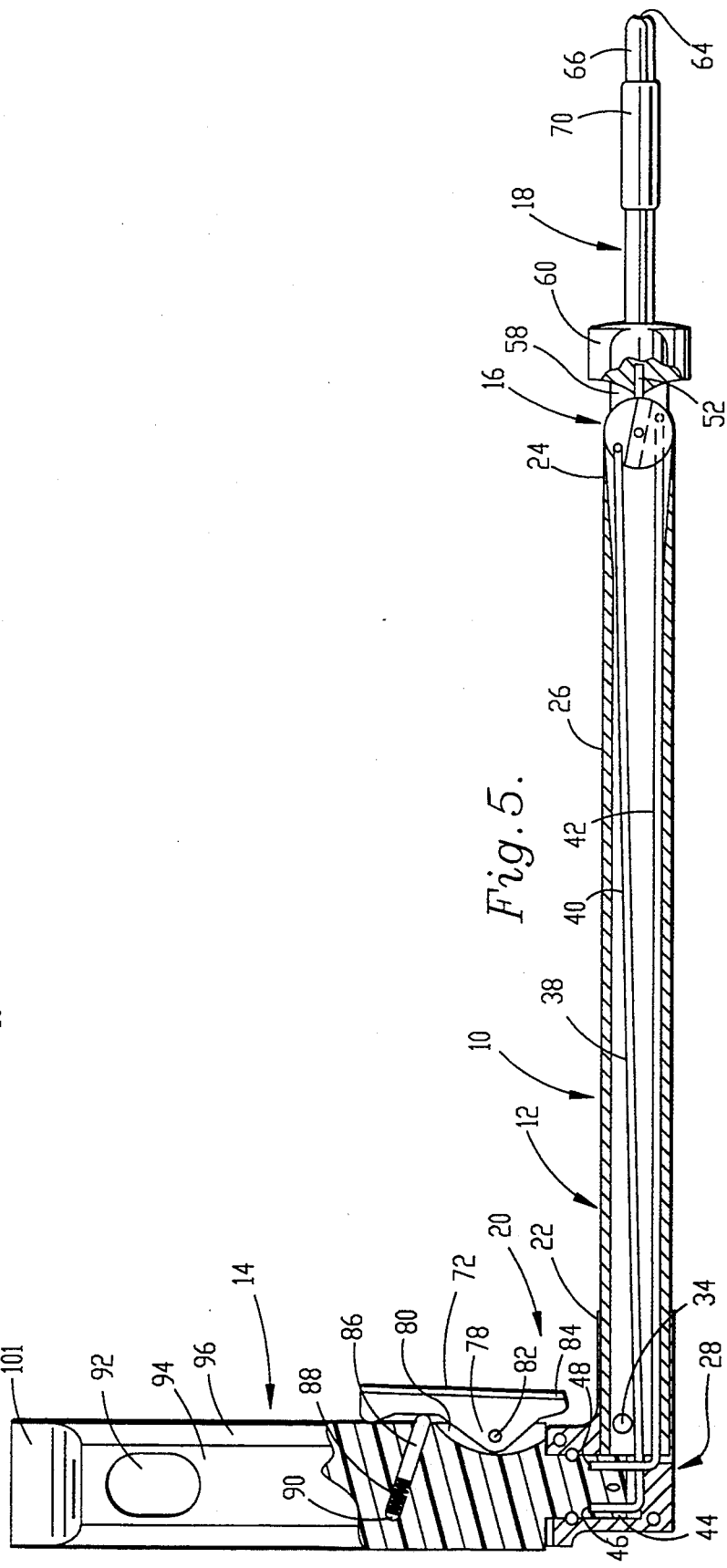

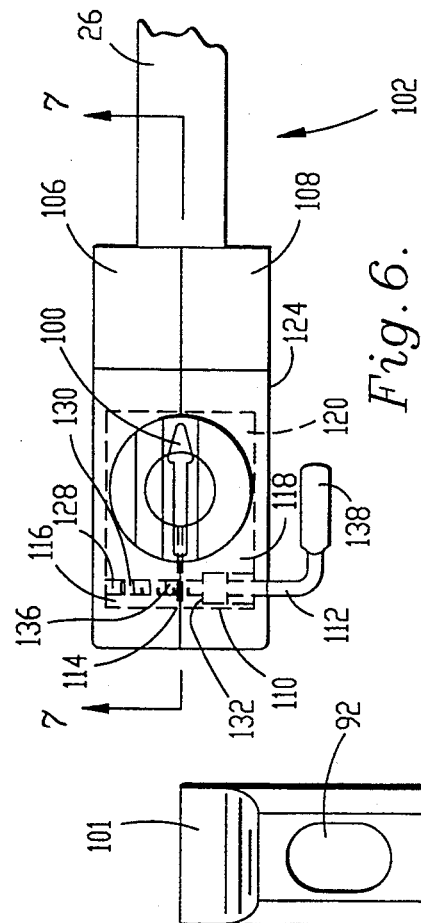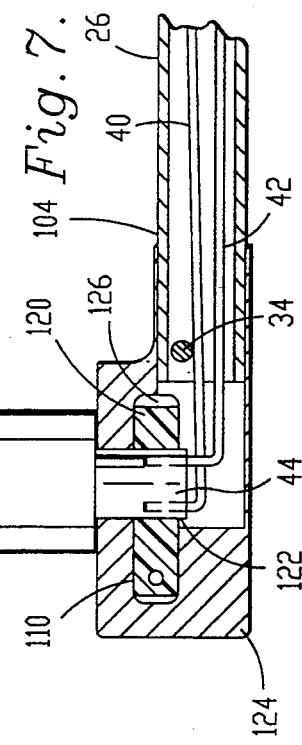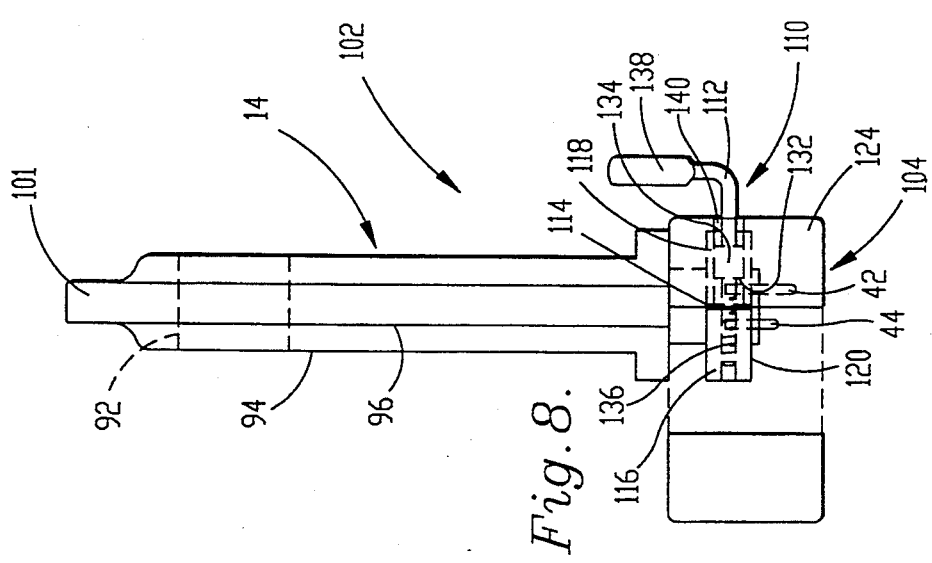

UTERINE MANIPULATOR WITH LOCKING MECHANISM

BACKGROUND OF THE INVENTION

1. Field of the Invention

This invention concerns a medical instrument used to manipulate a uterus during laproscopic examination or surgery a method associated therewith, The instrument is designed to receive a manipulating element or tip which may be pivoted relative to the frame of the instrument by turning a handle, the device including a locking mechanism for holding the handle and thus the tip in a desired position, 2. Description of the Prior Art Gynecologists frequently examine the internal pelvic organs of a patient by using a laparoscope. The medical procedures may include laproscopic tubal occlusion and fertility studies. During such laproscopic procedures, it is frequently necessary for the uterus to be repositioned in order to obtain an X-ray or to perform surgery.

Instruments have been developed to aid the surgical team in these procedures, and particularly to manipulate the uterus into a desired orientation. Typically, these instruments involve a tip or hook which is pivotally mounted on a frame and which can be manipulated by a handle of some type positioned remote from the tip. The devices are used by inserting the tip through the vaginal canal until reaching the uterus. With the tip engaging the uterus, medical personnel shift a handle or the like on the portion of the device then exterior to the patient's body, which in turn raises the uterus into position. Such devices are shown by, for example, U.S. Pat. Nos. 4,022,208 to Valtchev and 4,085,756 to Weaver.

More recently, a uterine manipulator has been developed which include a rotatable handle which serves to actuate and orient the tip of the device. Such an instrument with a rotatable handle is enjoying increased popularity, but has a disadvantage in that while it is provided with detents to audibly signal reorientation of the tip, the detents fail to engage with sufficient force to hold the tip, and therefore the uterus, in position. Consequently, a nurse or physician is compelled to hold the handle against undesired turning to prevent movement of the uterus, producing fatigue as well as preventing use of the hand for other tasks.

In addition, the task to be performed by such devices, while important, is mechanically fairly simple. In many instances, it may be more economical to provide a simplified device which may be inexpensively constructed and disposed of after use rather than undergoing rigorous sterilization procedures. Nonetheless, such disposable instruments nonetheless would preferably include some type of locking mechanism to prevent undesired movement of the handle connected to the tip.

A further observation which has been made about the current uterine manipulating devices is that they fail to provide a visually perceptible indication of the orientation of the tip and therefore the uterus relative to the remainder of the instrument. Since the tip is positioned entirely interior to the patient's body during use, it is often difficult or impossible for the physician to know, at a glance, the degree to which the uterus has been moved from the normal position. A need has therefore developed for a uterine manipulation device which includes a means for visually or tactilly perceiving the orientation of the tip by viewing the position of the handle relative to the frame.

SUMMARY OF THE INVENTION

These and other needs are to a significant degree met by the uterine manipulation device of the present invention. That is to say, the uterine manipulation device hereof includes a selectively actuatable locking mechanism which holds the rotatable handle in a desired orientation relative to the frame.

As in the prior art, the uterine manipulation device hereof preferably includes a frame, a graspable handle pivotally mounted on the frame, and a mount carried by the frame for pivotal movement relative thereto. The mount is operatively coupled to the handle by shifting structure, whereby a tip positioned on the mount may be inserted into the uterus for manipulating the latter by turning the handle. In the present invention, a locking mechanism is preferably provided which positively locks the handle, thereby holding the tip against undesired movement. The locking mechanism may comprise, for example, a clamp carried by the frame to tighten the latter around the handle, or alternatively a latching mechanism which may be positioned in one of a plurality of recesses to hold the handle and therefore the tip in a desired position. The latch thereby locks the handle relative to the frame to prevent undesired movement but may be readily released by the thumb or finger of the user so as to leave the other hand free.

Another advantage of the present invention is the provision of a visible or tactile indicator on the handle to provide an indication of the degree of pivoting of the tip relative to the handle. Unlike the prior art, the handle is preferably shaped to provide an indication of the amount of tip deflection. For example, the handle may be eccentric or flattened on one or more sides, the amount of turning of the handle relative to the frame corresponding to the amount of deflection of the tip relative to the frame. The user can tell the amount of deflection immediately and without looking just by feeling where the flattened side or side is positioned. Alternatively or in addition, an arrow or other visual indicator can be position, e.g. on the bottom of the handle. The user can quickly see the degree of deflection by seeing the position of the arrow relative to the frame. This presents obvious advantages in that it has heretofore been difficult for the surgeon to immediately detect the amount of deflection of the tip since the handle was basically without any visual or tactile indicator.

A further advantage of the present invention over the prior art is the inclusion of an opening in the handle capable of receiving flexible material therethrough. This opening is of a dimension sufficient to allow surgical gauze or other similar flexible supporting material to pass therethrough so that the uterine manipulation device may be temporarily supported by the gauze tied or otherwise attached to the patient's legs during examination or surgery in accordance with the method hereof. This leaves the physician's or nurse's hands free to perform other tasks.

These and other advantages may be recognized by those skilled in the art with reference to the following detailed description of the attached drawings.

BRIEF DESCRIPTION OF THE DRAWINGS

FIG. 1 is a right side elevational view of a first embodiment of the present invention;

FIG. 2 is a right side foreshortened elevational view of the invention of FIG. 1 in partial section with the handle and tip pivoted 90° from the position shown in FIG. 1;

FIG. 3 is a foreshortened bottom plan view of the invention of FIG. 1 with portions of the handle broken away to show the locking mechanism with the tip removed and the handle rotated to a position intermediate that shown in FIGS. 1 and 2;

FIG. 4 is a bottom plan view of the invention of FIG. 1 showing the indicator on the handle with the handle and tip in the position shown in FIG. 2;

FIG. 5 is a right side elevational view in partial section of the invention of FIG. 1 showing the structure connecting the handle to the mounting member for carrying the tip;

FIG. 6 is a fragmentary bottom plan view of an alternate embodiment of the present invention showing a locking screw for selectively locking the handle in position;

FIG. 7 is a fragmentary side elevational view of the embodiment of FIG. 6 showing the frame in partial section;

FIG. 8 is a rear end elevational view of the second embodiment of the present invention showing one-half of the frame separated and exploded from the other half of the frame.

DESCRIPTION OF THE PREFERRED EMBODIMENT

Figure 9:
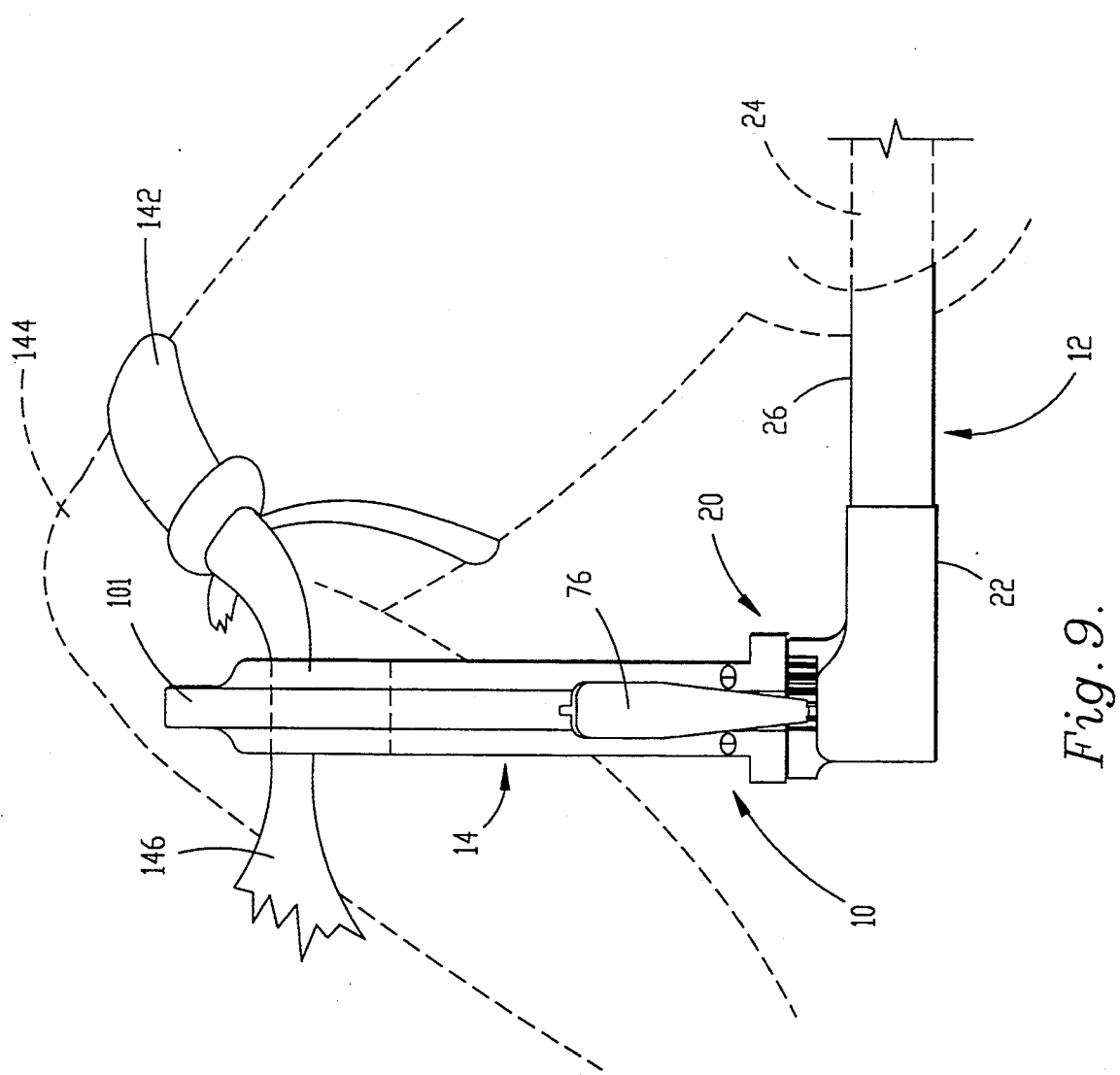
FIG. 9 is a fragmentary right side elevational view similar to FIG. 1, but illustrating the method of the present invention using material tied around a patient's legs to support the device during examination or surgery.

Referring now to the drawings, a uterine manipulator 10 is shown in FIGS. 1-5 which broadly includes a frame 12, a handle 14, a tip mount 16 adapted to removably receive thereon a uterine manipulating tip 18, and a locking mechanism 20. The frame 12 defines a proximate end 22 to which the handle is affixed and a remote end 24 for receiving thereon the tip mount 16. It will be readily appreciated that the remote end 24 is to be inserted into the vaginal cavity of a patient during use of the uterine manipulator 10 during examination or surgery, while the proximate end 22 remains exterior to the patient's body.

In greater detail, the frame 12 includes an elongated tubular housing 26 extending between a the proximate end 22 and the remote end 24. The housing 26 is inserted into a head 28 which couples the frame 12 to the handle 14. The head 28 is preferably formed into first half 30 and second half 32 which are held together by a screw 34 or other fastener. Slots 35 are provided in the remote end 36 which serves as a yoke to pivotally receive tip mount 16 therein. As may be seen in FIG. 5, housing 26 surrounds connecting structure 38 which operatively couples tip mount 16 to handle 14. Connecting structure 38 includes guide wires 40 and 42 which are connected to and extend from opposite sides of the substantially cylindrical tip mount 16 to a receiver 44 on the handle 14. The receiver 44 projects from the remainder of the handle into the interior of the head 28 and includes bores 46 and 48 which receive the proximate ends of the guide wires 40 and 42 therein.

The tip mount 16 includes a hole 50 for receiving therein a guide wand 52 projecting from the tip 18. A mounting post 54 extends axially through the tip mount 16 and outwardly from the sides of the remote end 24 of the frame 12. The mounting post 54 serves both to locate the tip mount in the longitudinally extending slots but also as an axis about which the tip mount 16 may pivot. Yet further, the mounting post serves to receive the flexible rearwardly projecting ears 56 and 58 of the tip thereon whereby the tip 18 may be removably mounted on the mounting post 54. The tip 18 may be pivoted about the mounting post 54 when the guide wand 52 is located in the hole 50 by turning the handle 14 to correspondingly move the tip mount. The tip 18 includes a natural or synthetic rubber body 60 with dye conduit 62 extending through the ear 56 for communicating with a tip bore 64 extending through finger 66. The tip also includes a balloon conduit 68 extending through ear 58 to communicate with an expandable balloon 70 surrounding the finger 66.

The description of the uterine manipulating device set forth above is known in the art. The uterine manipulating device 10 differs substantially in one respect therefrom in the inclusion of locking mechanism 20 which serves to connect and fix the handle 14 relative to the frame 12. The locking mechanism of the embodiment shown in FIGS. 1-5 includes latch 72 which is pivotally mounted to the handle 14 and engages a selected one of a plurality of slots 74a, 74b, 74c, 74d, 74e or 74f in the head 24 immediately adjacent the handle 14. The slots 74a-f are positioned at about 14° intervals to provide a satisfactory incremental range through which the handle 14 and correspondingly the tip 18 may be locked. The latch 72 could also be mounted to the frame 12 and engage selected slots in the handle, but as shown herein there is some advantage in use to locating the latch 72 on the handle.

The latch 72 preferably includes a leg 76 on which the users thumb may be placed, a shoulder 78 positionable within a groove 80 in the handle 14 and adapted to receive a pivot pin 82 therethrough, and boss 84 for positioning in one of the slots 74a-f to lock the handle 14 relative to the frame 12. The groove 80, best seen in FIG. 5, permits the shoulder 78 to rock about the pivot pin 82, thereby permitting the boss 84 to swing free of the head 24 so that the handle 14 may be pivoted as desired before locking. The latch 72 is also engaged by biasing rod 86 urged toward the latch 72 by a spring 88. The biasing rod 86 and spring 88 are directed toward latch by the complementally configured guide hole 90 defined in handle 12.

The handle 14 also presents structure defining a passageway 92 oriented and extending transversely therethrough. The passageway 92 is substantially enclosed by the handle 14, although it may be appreciated that a small gap would be an acceptable equivalent which would allow gauze or other fabric to be inserted therethrough and held during use of the uterine manipulator 10.

Handle 14 is also preferably configured with one or more flattened sides 94 which provide an identifiable tactile indication of the orientation of the handle 14 relative to the frame 12. Thus, as may be seen in FIG. 4, the handle 14 is elongated in its longest dimension along its graspable portion 96. As a further orientation indicator, indicia 98 in the form of arrow 100 is written onto or preferably molded or cast into the narrowed, orientation-indicating top 101 of the handle whereby the user may have an immediate indication of the orientation of the handle 14 relative to the frame 12. Since the handle 14 is directly operatively coupled to the tip mount 16 and tip 18 mounted thereon by connecting structure 38, the arrow 100 also serves to indicate the orientation of the tip mount 16 and tip 18 relative to the frame 12.

Uterine manipulator 102 represents an alternate embodiment of the present invention. Whereas uterine manipulator 10 is preferably made primarily of stainless steel or aluminum and designed for reuse after sterilization, the uterine manipulator 102 is made of synthetic resin and thus may be more economically disposed instead of cleaned, sterilized and reused. The uterine manipulator 102 is provided with a remote end which is substantially the same as the remote end 24 and includes a tip mount 16 for receiving a tip 18 thereon. However, the frame 104 of the uterine manipulator 102 may be formed from first half 106 and second half 108 of synthetic resin which may be glued or otherwise bonded together.

The locking mechanism 110 of the uterine manipulator 102 includes a locking lever 112 which is threadably inserted across the gap 114 and into the arms 116 and 118 of C-shaped lock block 120. The block 120 is preferably made of a synthetic resin such as nylon and includes a circular central opening 122 for receiving therein the receiver 44 of the handle 14. The handle 14 is preferably constructed of synthetic resin material and is substantially the same as the handle 14 of the first embodiment shown in FIGS. 1–5.

The frame 104 includes a head 124 for receiving the receiver 44 of the handle 14 therein. The head 124 is also internally configured for holding the block 120 in position. Thus, the head 124 includes a recess 126 defined in each the first half 106 and the second half 108 thereof which is complementally configured with the external dimensions of the block 120 to prevent undesired turning of the block 120 within the frame 104 when the first half 106 is joined to the second half 108.

The block 120 is provided with a transversely extending bore 128 which includes a threaded portion 130 on arm 116 and a shoulder 132 on arm 118. The shoulder 132 engages a circumscribing rim 134 on locking lever 112 which includes a threaded section 136 and a lever arm 138. The threaded section 136 is preferably of a triple lead screw type which allows the block 120 to clamp tightly on the receiver 44 in only 60° to 90° of movement. An access 140 is provided through second half 108 of the frame 104 in the head 124 to permit passage of the locking lever 138 into the block 120.

Use of the uterine manipulators 10 and 102 is in large part similar to those of the prior art. The patient positions herself for a pelvic examination and the physician attaches a tip 18 to the mount 16 on the uterine manipulator, connecting the conduits 62 and 68 to respective sources of dye and pressurized gas, as desired. The physician then inserts the uterine manipulator into the pelvic region until the finger 66 enters the uterus. The uterine manipulator is inserted with the finger 66 aligned with the frame 12 or 104, and the handle oriented generally upwardly so that the arrow 100 is visible to the physician. When the physician desires to manipulate the uterus into an anterior orientation, the handle 14 is rotated in a clockwise direction. The handle 14 is directly coupled to the mount 16 and therefore the tip 18, so that rotation of the handle 14 produces a corresponding and equal angular displacement of the tip. FIGS. 2, 4 and 5 shows the uterine manipulator in the initial entry position with the arrow 100 of the handle 14 aligned with the frame 12 and the finger 66 of the tip 18 also extended forwardly in alignment with the frame 12. This may be contrasted with the position of the finger 66 shown in FIG. 1, where the handle 14 has been rotated 90° from the initial entry position resulting in the tip 18 also pivoting and elevating 90° from its initial position.

However, because of the direct connection between the handle 14 and the tip mount 16 and tip 18, absent a locking mechanism, release of the handle 14 may also allow the tip 18 to return to its initial entry position when so urged by the uterus of the patient. Locking mechanisms 20 or 110 serve to prevent an undesired return.

During rotation of the handle 14 of uterine manipulator 10, the physician depresses the leg 76 to cause the boss 84 of the latch 72 to remain clear of the slots 74a–f. When the uterus is properly positioned, the physician need only release the leg 76 to thereby cause the boss 84 to be urged by the spring 88 and biasing rod 86 into a selected one of slots 74a–f. The physician can readily affirm the orientation of the finger 66 of the tip 18 (and therefore the uterus) by viewing the arrow 100 and comparing the angular displacement of the handle 14 relative to the elongated housing 26 of the frame 12. The physician also may tactilely compare the deflection by feeling the shape of the handle 14 and comparing the elongated flattened sides to the orientation of the housing 26.

During the examination, the physician may find it advantageous to use both hands to perform some task while maintaining the uterus in an elevated (anterior) orientation. This may be easily accomplished by running a length of surgical gauze or other material 142 between the patient's knees 144 and through the passageway 92 as shown in FIG. 9. By tying the gauze to the patient's knees 144, the uterine manipulator 10 or 102 may be temporarily suspended with the uterus still repositioned. It is to be understood from FIG. 9 that the material is tied to each of the patient's knees, with only one end of the material 142 being fully displayed in a knotted position, and that the other end 146 would be similarly tied to the opposite knee. The remote end 24 of the housing 26 is inserted into the vaginal cavity of the patient as illustrated, with the handle 14 and locking mechanism remaining exterior thereto. The free ends of the material 142 may be adjusted in a selected position as desired by the physician.

If the uterine manipulator 102 is to be used, the locking mechanism 110 operates in much the same manner, except that the physician has complete flexibility of location in that the handle 14 can be clamped at any location within its range of movement. While holding the handle 14, the physician turns locking lever 134 which decreases the gap 114 and brings the arms 116 and 118 together. This serves to clamp the receiver 44 and thus prevents the movement of the mount 16 or tip 18 operatively connected thereto. When the procedure or examination is completed, the physician releases the clamping action by turning the locking lever 134 in the opposite direction and brings the handle 14 to its initial entry position for removal of the uterine manipulator from the patient's pelvic region.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of their invention as pertains to any apparatus not materially departing from but outside the liberal scope of the invention as set out in the following claims.

We claim:

1. In a uterine manipulating device having an elongated frame presenting a longitudinal axis and having a remote end and a proximate end, at least one connecting member received within said frame, a tip mount shiftably carried at the remote end of the frame actuatably connected to said connecting member for shiftable moving an elongated uterine manipulating member thereon within a plane oriented substantially perpendicular to said longitudinal axis, and a graspable handle tip mount to said frame and operatively connected to said tip mount by said connecting member, said handle being mounted for pivotal movement about a pivot axis transverse to said longitudinal axis and substantially parallel to said plane, wherein the improvement comprises a locking member including a latch member pivotally mounted to one of said handle and said frame adjacent the proximate end of said frame for direct locking engagement with the other of said handle and said frame for thereby selectively locking said handle relative to said frame and for correspondingly maintaining said tip mount in a desired, shifted orientation, said locking member further including a spring for biasing the latch member into direct locking engagement with a selected one of a plurality of recesses defined in the other of said handle and said frame.

2. In a uterine manipulating device having an elongated frame presenting a longitudinal axis and having a remote end and a proximate end, at least one connecting member received within said frame, a tip mount shiftably carried at the remote end of the frame actuatably connected to said connecting member for shiftable moving an elongated uterine manipulating member thereon within a plane oriented substantially perpendicular to said longitudinal axis, and a graspable handle mounted to said frame and operatively connected to said tip mount by said connecting member, said handle being mounted for pivotal movement about a pivot axis transverse to said longitudinal axis and substantially parallel to said plane, wherein the improvement comprises:

a locking member pivotally mounted to said handle adjacent the proximate end of said frame for direct locking engagement with said frame, said locking member including a latch member pivotally mounted to said handle, said latch presenting a boss located proximate said frame and a leg for receiving a human digit thereon, said locking member further comprising a pivot pin pivotally mounting said latch member to said handle, said locking member further including a spring biasing said boss into direct locking engagement with said frame and a plurality of circumferentially spaced slots on said frame complementally configured to receive said boss in locking engagement therewith.

* * * * *